United States Patent
Kumar et al.

(10) Patent No.: US 10,758,653 B2
(45) Date of Patent: Sep. 1, 2020

(54) AUTOMATED COMPRESSION NURSING AND PUMPING SYSTEM

(71) Applicant: LILU, INC., Brooklyn, NY (US)

(72) Inventors: Sujay Suresh Kumar, New York, NY (US); Adriana Catalina Vazquez Ortiz, New York, NY (US)

(*) Notice: Subject to any disclaimer, the term of this patent is extended or adjusted under 35 U.S.C. 154(b) by 0 days.

(21) Appl. No.: 16/424,766

(22) Filed: May 29, 2019

(65) Prior Publication Data
US 2019/0275221 A1 Sep. 12, 2019

Related U.S. Application Data

(63) Continuation-in-part of application No. 15/598,050, filed on May 17, 2017, which is a continuation of application No. 15/373,752, filed on Dec. 9, 2016, now abandoned.

(60) Provisional application No. 62/419,747, filed on Nov. 9, 2016.

(51) Int. Cl.
*A61M 1/06* (2006.01)
*A41C 3/04* (2006.01)
*A41C 3/10* (2006.01)

(52) U.S. Cl.
CPC .............. *A61M 1/062* (2014.02); *A41C 3/04* (2013.01); *A41C 3/105* (2013.01)

(58) Field of Classification Search
CPC ........ A61M 1/06; A61M 1/062; A61M 1/064; A61M 1/066; A61M 2209/088; A61H 2205/082; A41C 3/04; A41C 3/0028
See application file for complete search history.

(56) References Cited

U.S. PATENT DOCUMENTS

| | | | |
|---|---|---|---|
| 4,551,874 A * | 11/1985 | Matsumura | A61H 9/0078 5/630 |
| 5,885,246 A * | 3/1999 | Ford | A61M 1/066 604/74 |
| 6,273,868 B1 | 8/2001 | Nordvik | |
| 6,383,164 B1 | 5/2002 | Johansen | |
| 2005/0234370 A1* | 10/2005 | Beal | A61H 9/0078 601/15 |
| 2008/0039781 A1* | 2/2008 | Bjorge | A61M 1/062 604/74 |
| 2014/0378946 A1* | 12/2014 | Thompson | A61M 1/062 604/514 |
| 2015/0065994 A1 | 3/2015 | Fridman et al. | |
| 2017/0112983 A1* | 4/2017 | Thorne | A61M 1/06 |

* cited by examiner

*Primary Examiner* — William R Carpenter
(74) *Attorney, Agent, or Firm* — Chan Hubbard PLLC; Keala Chan (57) ABSTRACT

A system for hands-free nursing and breast pumping includes a breast compression device with a plurality of thermoformed fluid bladders designed to fit adjustably against each breast and inflate and deflate with minimal power requirements. The compression device and its controller fit inside of a nursing garment designed to receive the device and controller for optimal compression. The nursing garment and the compression device have openings over the nipples so that a breast pump flange can be inserted through them and used in a typical manner for the extraction of breast milk, thus increasing the amount of milk expressed.

9 Claims, 10 Drawing Sheets

AUTOMATED COMPRESSION NURSING AND PUMPING SYSTEM

CROSS-REFERENCE TO RELATED APPLICATIONS

The present application claims the benefit of U.S. Utility patent application Ser. No. 15/598,050, filed May 17, 2017, which is a continuation of U.S. Utility patent application Ser. No. 15/373,752, filed Dec. 9, 2016, which claims the benefit of U.S. Provisional Patent Application 62/419,747, filed Nov. 9, 2016. The contents of those applications are hereby incorporated by reference.

BACKGROUND

It is known that manual breast massage increases the amount of milk expressed in a breastfeeding session (Bowles, B. C. (2011). Breast Massage: A "Handy" Multipurpose Tool to Promote Breastfeeding Success. *Clinical Lactation*, 2(4), 21-24.). Health benefits of compression massage during breastfeeding or breast pumping include preventing and relieving mastitis, plugged ducts, and engorgement (Witt, A. M. et. al. (2016). Therapeutic Breast Massage in Lactation for the Management of Engorgement, Plugged Ducts, and Mastitis. *Journal of Human Lactation*, 32(1), 123-31.). When combined with electric pumping, manual massage both increased milk production (Morton, J. et. al. (2009). *Journal of Perinatology*, 29, 757-64.) and caloric content (Morton, J. et. al. (2012). *Journal of Perinatology*, 32, 791-96.) for preterm infants. The benefit is not limited to preterm infants, however. Compression stimuli around the areola increases breast pump efficiency more generally by stimulating the release of necessary hormones (Alekseev, N. P. et. al. (1998). Compression stimuli increase the efficacy of breast pump function. *European Journal of Obstetrics & Gynecology and Reproductive Biology*, 77(2), 131-39.). While manual massage has been used for centuries, the ability to pump efficiently hands-free would greatly improve the modern mother's productivity.

There are existing systems that combine hands-free compression and pumping. U.S. Pat. No. 6,213,840 B1, for example, discloses a simple hands-free bra that supports a breast pump system. It does not, however, address the need for compression. Some breast pumps have been designed to mimic manual compression, such as that described by the application US 2005/0234370 A1, which discloses that pressure is applied by a "plurality of opposing pairs of expression bellows." At least two patent applications describe hands-free compression systems to be used in conjunction with breast pumps using pneumatic modes of compression (US 2014/0378946 A1 and US 2015/0065994 A1). However, the prior art does not incorporate systems or methods that effectively mimic the best practices of manual compression, as indicated by research and expertise of lactation specialists, in an efficient device with low power requirements.

SUMMARY

The present invention addresses the needs in the prior art by providing rotating compression pressure across multiple areas of the breasts, more closely mimicking manual compression. The system and methods described herein further incorporate the existing research and existing expertise of lactation specialists to provide a controllable, hands-free compression and breast pumping system.

In particular, the system described herein provides hands-free expression of milk from human breasts in a rotating manner across multiple areas of the breast to mimic natural manual compression. The system comprises a compression device, a controller that controls the compression device, and a specialized garment for receiving the compression device, the controller and breast pump flanges. The compression device is comprised of a left and a right adjustable breast pad, each breast pad having a plurality of bladders whose inner surfaces comprise a plurality of ridges that perform massage effects on the breasts as the bladders are inflated and deflated by the controller. The compression device is actuated through fluid tubes that pass from the controller into the plurality of bladders of the compression device. The controller increases or decreases the pressure exerted by the compression device by increasing or decreasing the amount of fluid introduced into the compression device, which then determines how much the bladders inflate into the breast.

BRIEF DESCRIPTION OF THE DRAWINGS

The present invention will be more fully understood from the detailed description below taken in conjunction with the accompanying drawings, in which.

DETAILED DESCRIPTION

Certain embodiments will now be described to provide an overall understanding of the principles of the structure, function, manufacture, and use of the devices and methods herein disclosed. One or more examples of these embodiments are illustrated in the accompanying drawings, briefly described above.

Figure 1:
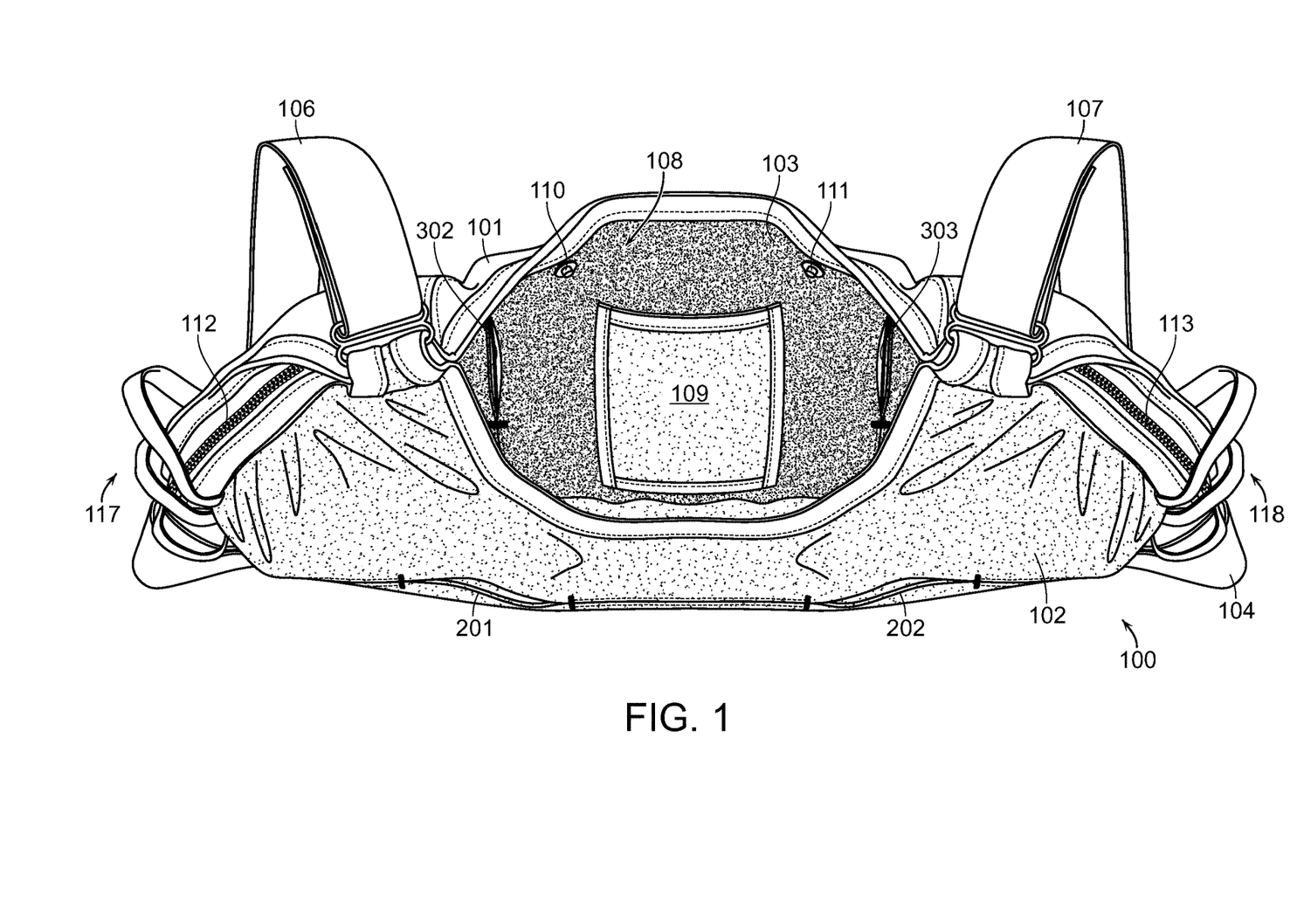
FIG. 1 is a top view of a garment that has been configured to accommodate a compression device and controller.
Figure 4:
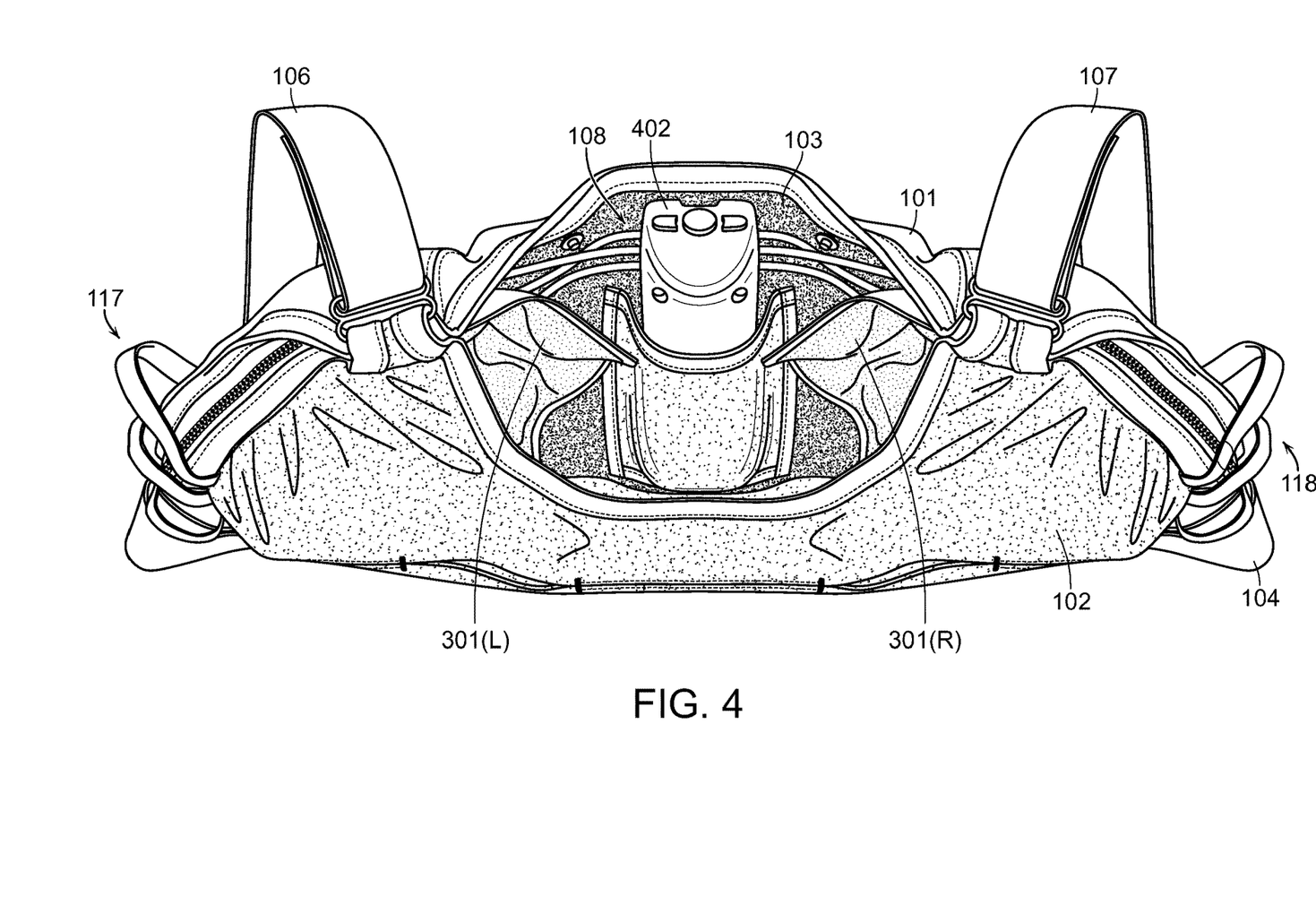
FIG. 4 is a top view of the garment with compression device and controller inside.

FIG. 1 is a top view of a garment [100], which has been configured to accommodate a compression device, a controller, and a breast pump. The garment comprises a bust cover comprising an outer layer [101], an inner layer [102] and a compression layer [103]; a torso band [104] binding the outer layer, inner layer and compression layer and having a closure means [105]; and a left [106] and right [107] shoulder strap connecting the bust cover to the torso band allowing the garment to be fastened in the back and worn as a bra. The combination of the inner layer [102] and compression layer [103] bound by the torso band [104] forms a pocket [108] for receiving the compression device [301]. FIG. 4 is a back top perspective view showing the compression device [301] and controller [402] within the pocket [108]. A holster located on the compression layer [103] holds the controller [402] in place over the breasts when worn, and as will be described further herein, positioning the controller [402] as such within the garment helps stabilize the compression device so that adequate compression can occur in and around the cleavage area of the breasts. It will be noted that the controller is small enough to fit within the holster [109] in the garment [100], and that the structure of the compression device [301] is designed to require minimal amounts of pneumatic or hydraulic power from the controller.

Figure 5:
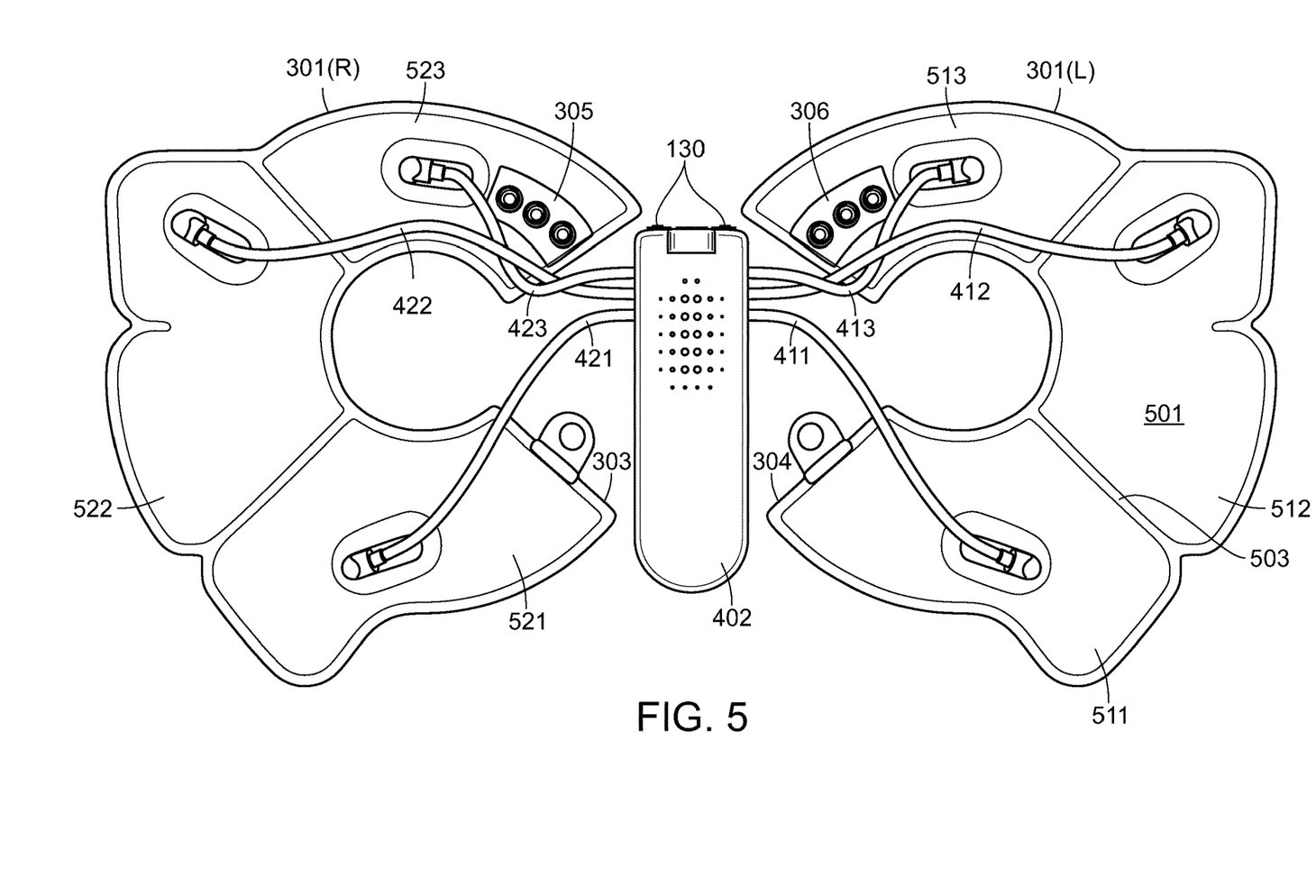
FIG. 5 is an anterior view of the compression device.
Figure 6:
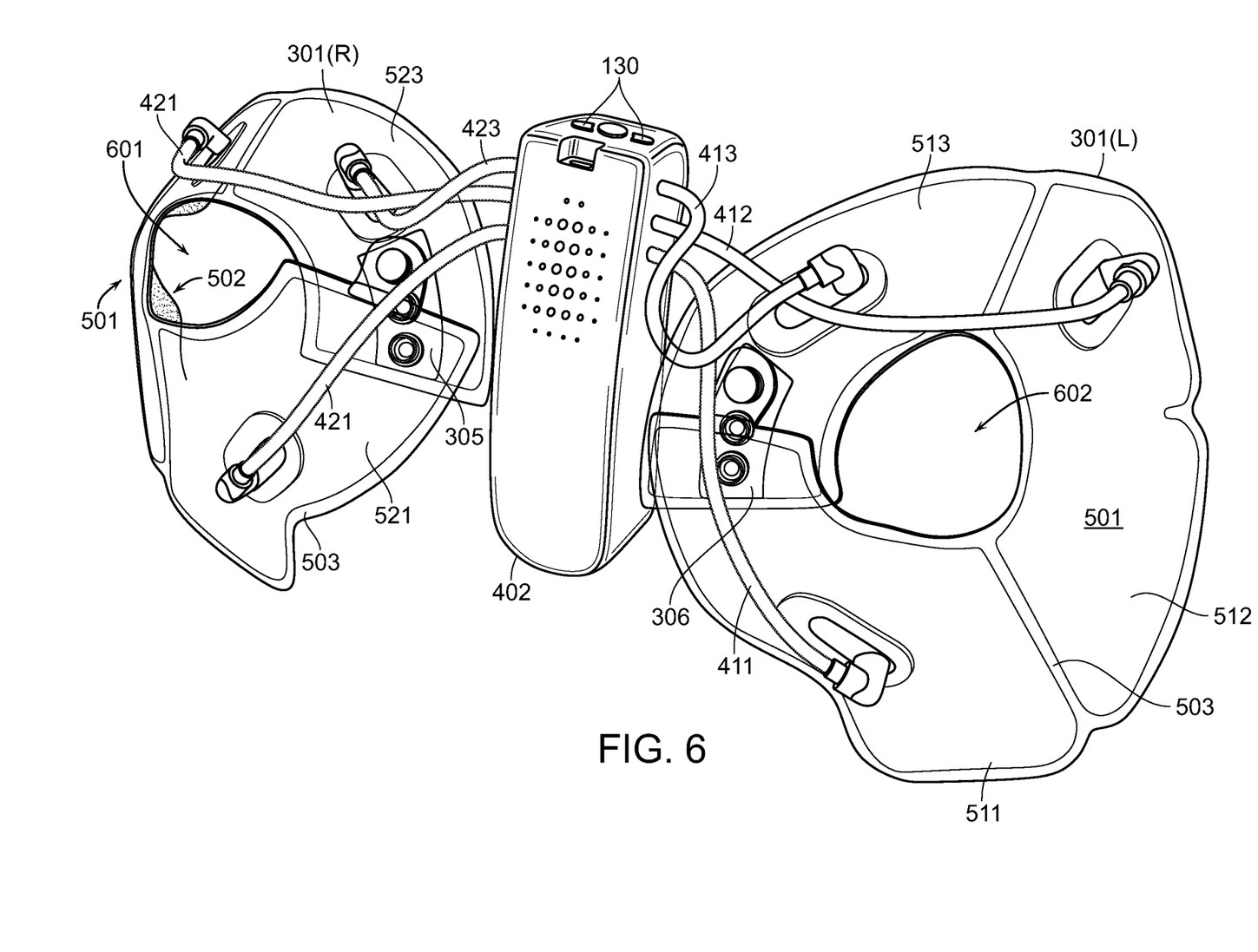
FIG. 6 is a perspective view of the compression device.

FIG. 5 and FIG. 6 are anterior and anterior perspective views of a compression device [301] and controller [402] suitable for use with garment [100]. The compression device is comprised of a left breast pad [301(L)] and a right breast pad [301(R)], each breast pad being a C-shaped pad with opening, and each breast pad comprising anterior and posterior [502] sheets, which are sealed [503] together such as to form a plurality of bladders [511-513; 521-523], each bladder supplied with a fluid supply tube [411-413; 421-423] at the anterior sheet [501]. The C-shape of breast pads enables size-adjustability of the breast pad, insofar as the open ends [303; 304] of a pad can be secured together using connection means [305; 306] such as buttons, causing the closed breast pad to form a frustum (see FIG. 6) that covers the breast. Adjusting the fastening means adjusts the central angle of the frustum which allows the breast pads to conform to various breast sizes and shapes. Further, the 'seals' [503] between bladders provide additional bending points to the bladder to increase ease of conforming to different breast sizes and shapes.

Figure 7:
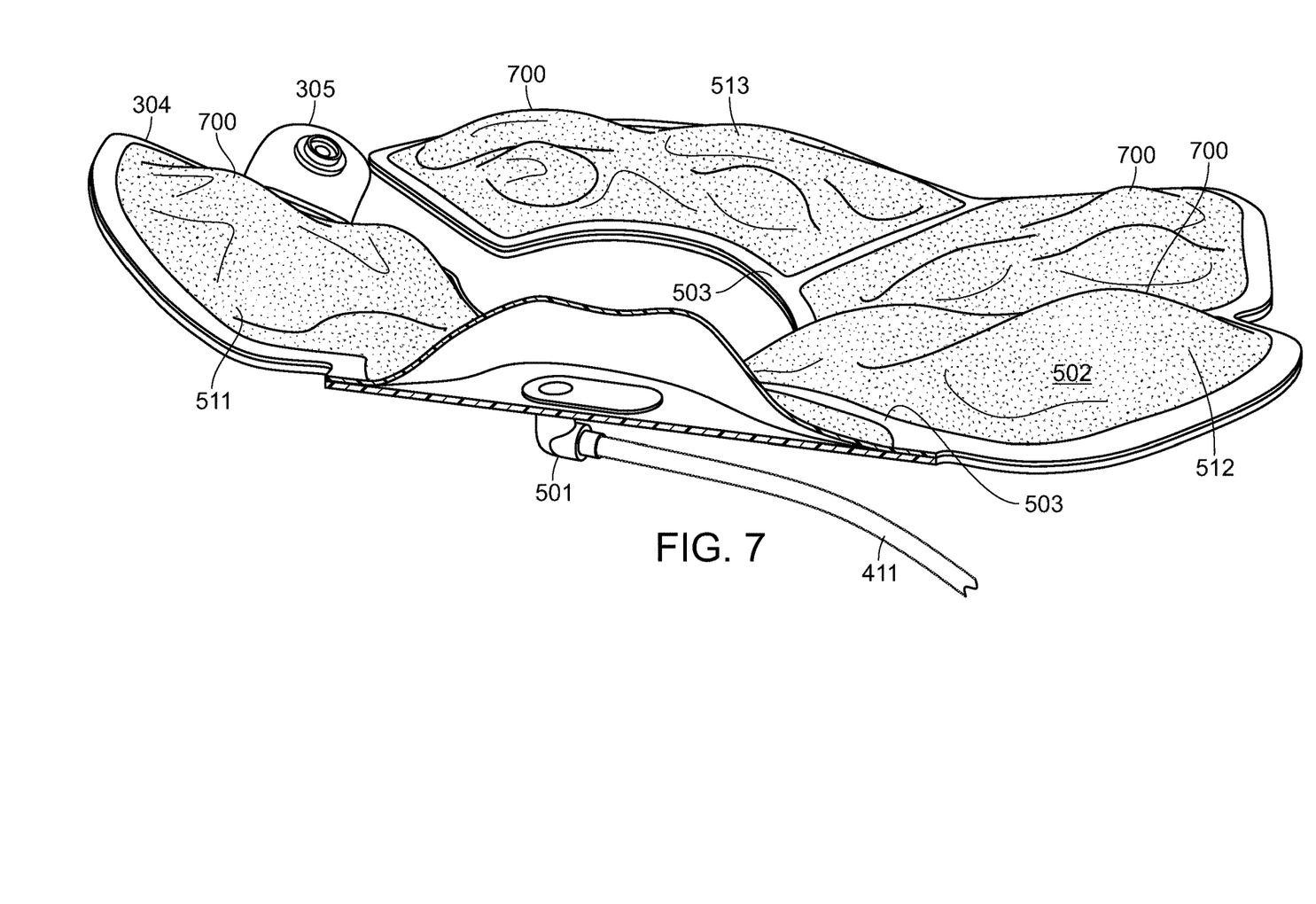
FIG. 7 is a side view of a breast pad of the compression device.

FIG. 7 is a side perspective view of a breast pad, partially opened to show the distinct anterior [501] and posterior [502] sheets, which are sealed [503] together to form the plurality of bladders [511-513]. Because the posterior [502] sheet faces the breast it is comprised of a malleable ridges [700] that perform the massage effect as the bladders are inflated and deflated. Preferably ridges [700] are thermoformed directly on the surface of the posterior sheets, but they may be comprised of any materials and formed by any process, such as elastic materials like silicone, rubber, or flexible plastic adhered to the surface of the posterior sheets using a high frequency welding process or the like. Ridges [700] that are thermoformed ensure partial inflation of the bladders, causing the bladders to inflate more quickly using the same amount of fluid compared to bladders without ridges. Ridges [700] comprised of an elastic material adhered to the surface improve efficiency of the device by mimicking massage motions even with partial inflation of the bladders. In order to ensure that posterior sheet [502] is inflated into the breast (instead of being pushed away from the breast), anterior sheet [501] is comprised of a malleable plastic thicker than posterior sheet [502]. The plurality of bladders can be formed by sealing [503] the anterior and posterior sheets together at any locations, such that bladders may be of different sizes and unlimited numbers.

Figure 8:
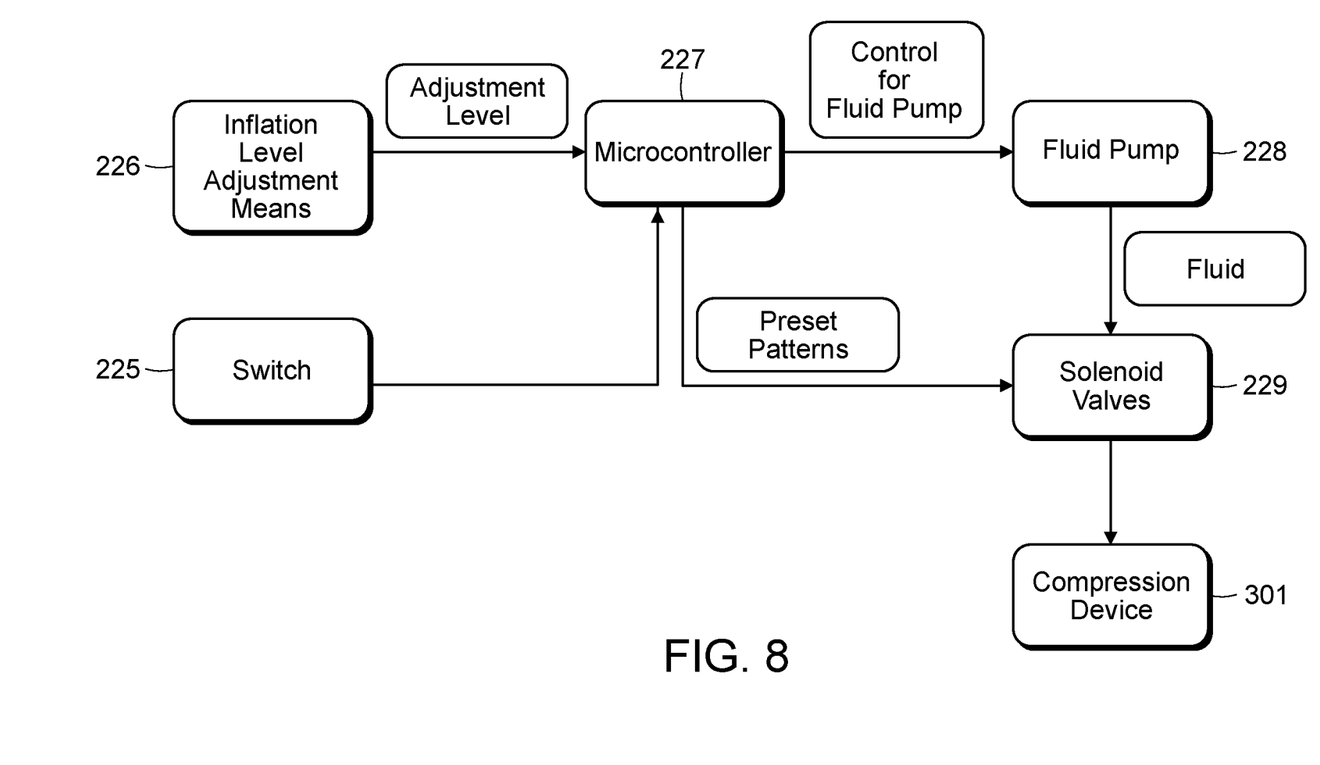
FIG. 8 is a high-level block diagram of the components operating the compression device.

With reference to FIG. 8, controller [402] comprises switch [225], inflation level adjustment means [226] to increase and decrease the inflation of bladders, microcontroller [227], fluid pump [228], and solenoid valves [229]. Switch [225] turns the device on or off by supplying or cutting off the supply of voltage. The inflation level adjustment means [226] may be adjustment buttons used to a) increase or decrease the pressure exerted by the compression device by increasing or decreasing the amount of the fluid pumped respectively and/or b) increase or decrease the duration for which the bladders inflate and deflate by increasing or decreasing the timing of the solenoid valves. The inflation level adjustment means [226] may be any mechanical means such as buttons or knobs for the user to increase or decrease the inflation level or frequency, said mechanical means in connection with a network of resistors which will adjust the voltage levels sent to the microcontroller [227]. Upon receiving these inflation settings for the bladders, microcontroller [227] controls the fluid pump [228] by adjusting the voltage required to power the pump. The source of the fluid used to inflate and deflate the bladders is the fluid pump [228]. The amount of fluid output by the pump [228] can be altered by altering the supply voltage of the pump. Microcontroller [227] controls both the fluid pump [228] and the solenoid valves [229]. Thus, microcontroller [227] can be programmed to inflate and deflate the bladders in different ways, for example, the bladders may be programmed to inflate and deflate in a rotational manner or they can be programmed to inflate and deflate simultaneously.

Solenoid valves [229] are electric valves that control the flow of fluid in and out of the bladders. When the valves [229] are turned on by the microcontroller [227], the fluid from the pump is sent to the compression device bladders via tubes [411-412; 421-423], causing the bladders [511-513; 521-523] to inflate. When the valves [229] are off, the fluid within the bladders is drained off from the solenoid valves, causing the bladders to deflate. By controlling these valves, the fluid supplied to the compression device can be turned on and off. The user can control the pressure exerted by the compression device by manipulating the inflation adjustment means [226].

Figure 9:
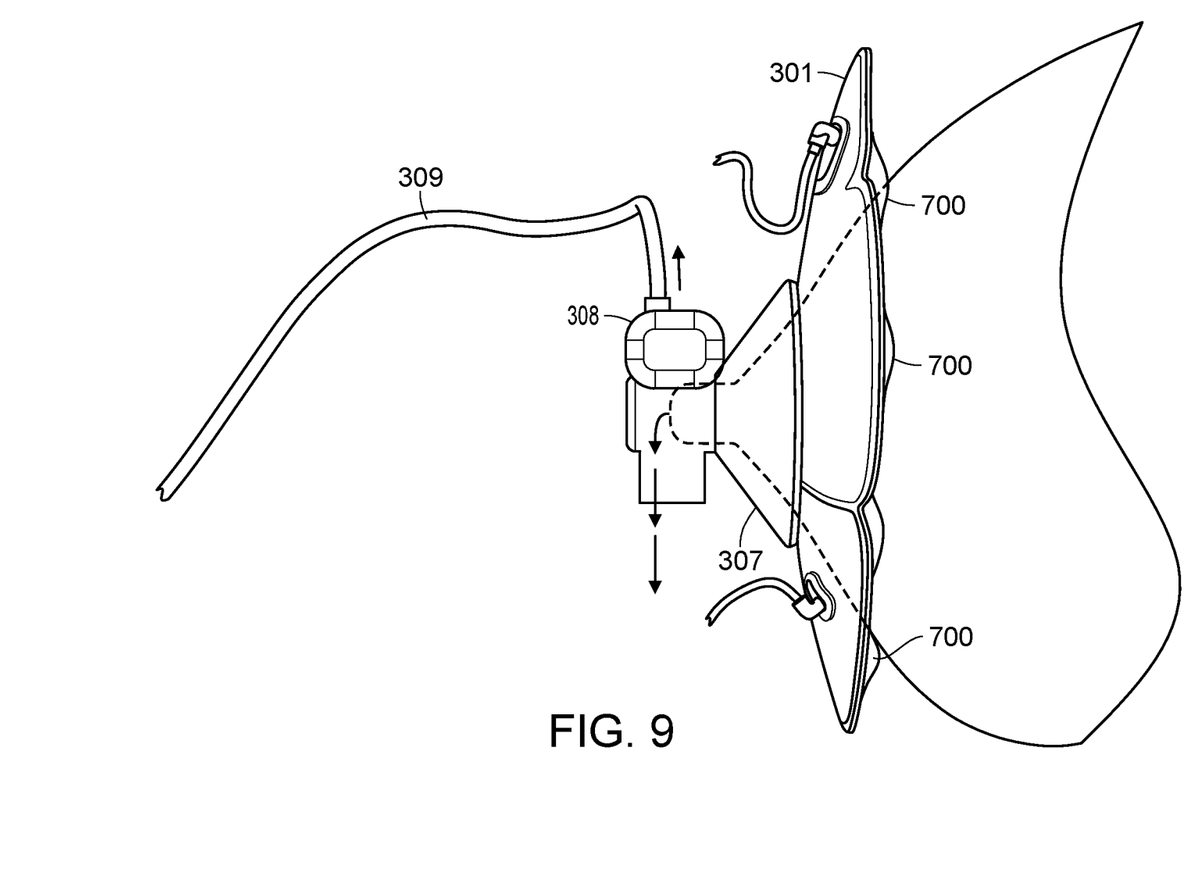
FIG. 9 is a side view of the compression device as it would lay on a user's breast, when used in combination with a breast pump.

As can be seen in FIG. 6, breast pads [301(L)] and [301(R)] are each formed into a frustum shape when closed by connection means [305; 306]. Connection means [305; 306] is preferably adjustable, using buttons, hook-and-loop fasteners or the like, thus allowing the breast pad to fit comfortably over different sized breasts. When closed, a breast pads forms an opening [601 or 602] at the upper part of the frustum, through which a breast pump flange of any size [701] can be accepted. By allowing the breast pump flange [701] to lay directly against the breast, a tight seal is formed between the breast pump and the breast. FIG. 9 is a side view of the compression device [301] and breast pump [308] atop a user's breast. Ridges [700] face the breast so that when the bladders inflate and deflate in a rotational manner, the ridges [700] apply pressure to the breast. FIG. 9 illustrates the placement of the nipple into the flange [307]. As air is suctioned out into an air tube [309], milk is expressed and collected into a milk storage unit in the direction shown.

Figure 2:
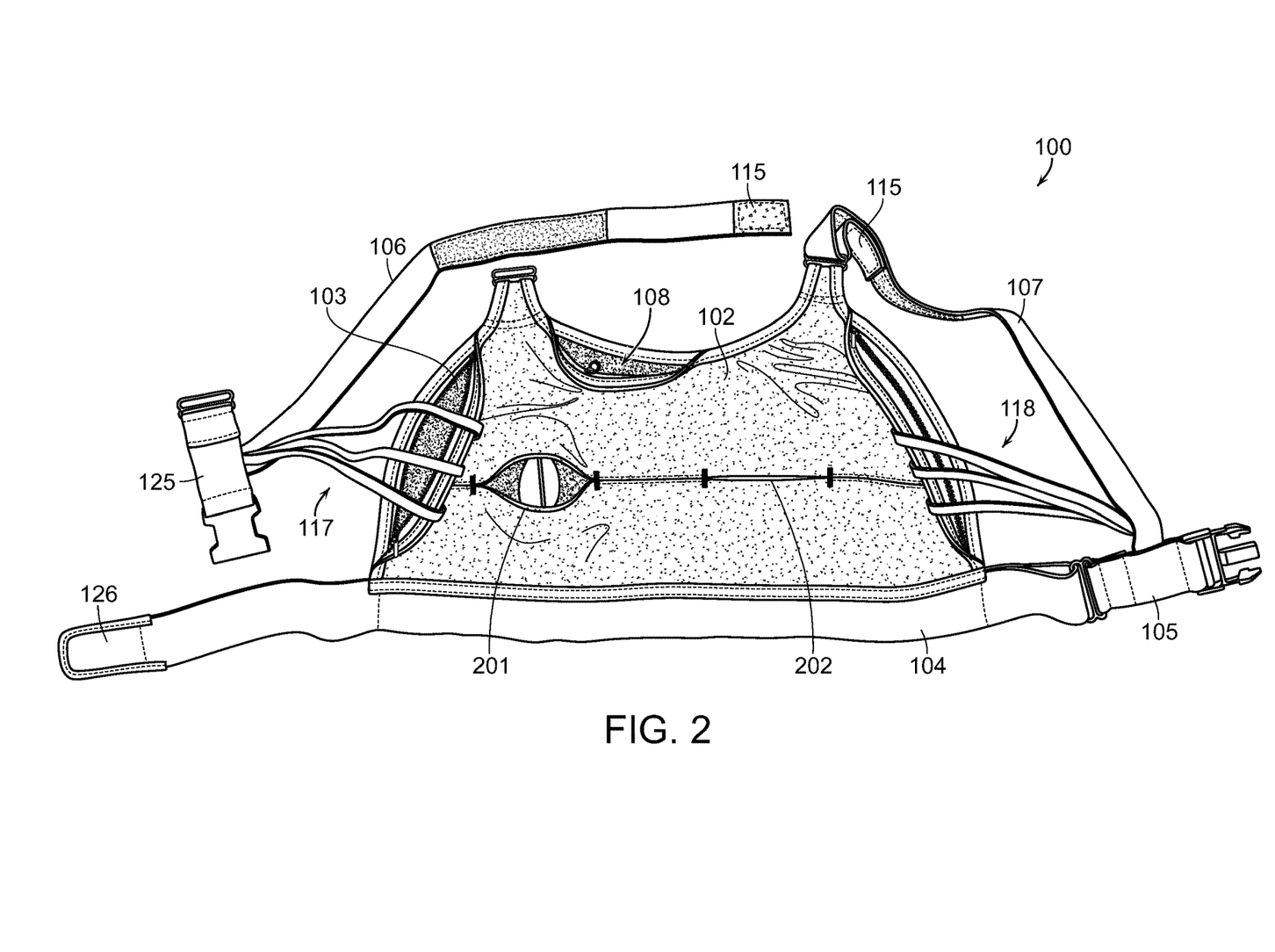
FIG. 2 is a posterior view of the garment.
Figure 3:
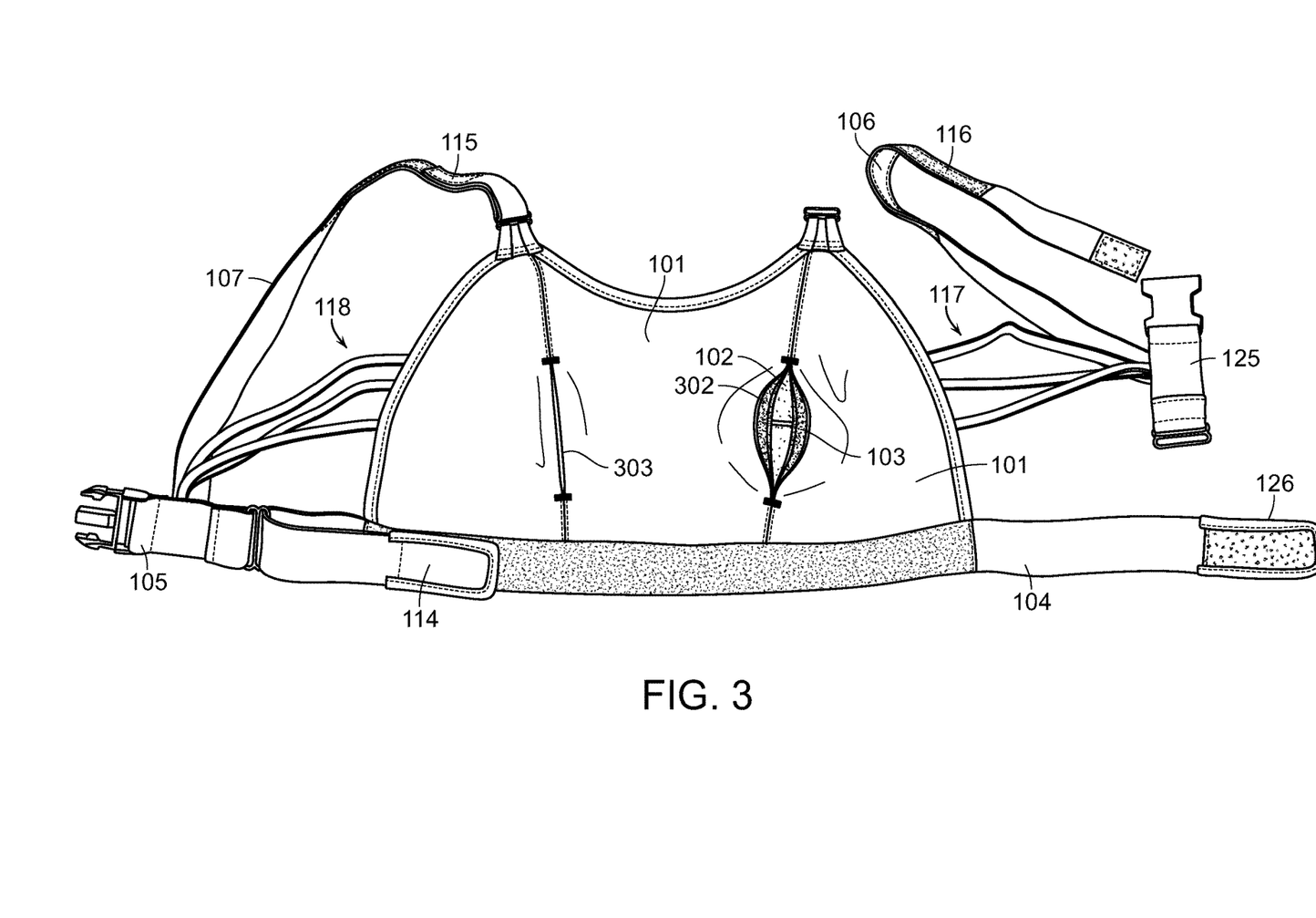
FIG. 3 is an anterior view of the garment.

As can be seen in FIG. 2 and FIG. 3, garment inner layer [102] comprises a horizontal opening [201; 202] in the area of each nipple, while outer layer [101] and compression layer [103] each comprise vertical openings [302; 303] in the area of each nipple. The positioning of said openings facilitate the easy attachment of the breast pump flange to the breast. The shape of said openings alternating between horizontal and vertical positioning furthermore ensures that the flange is held snugly in place without moving. Small cuts made on the seals of the compression pads further facilitate the attachment and compatibility with breast pump flanges of different sizes and allows for breast flanges to be inserted from either the front or back.

Figure 10:
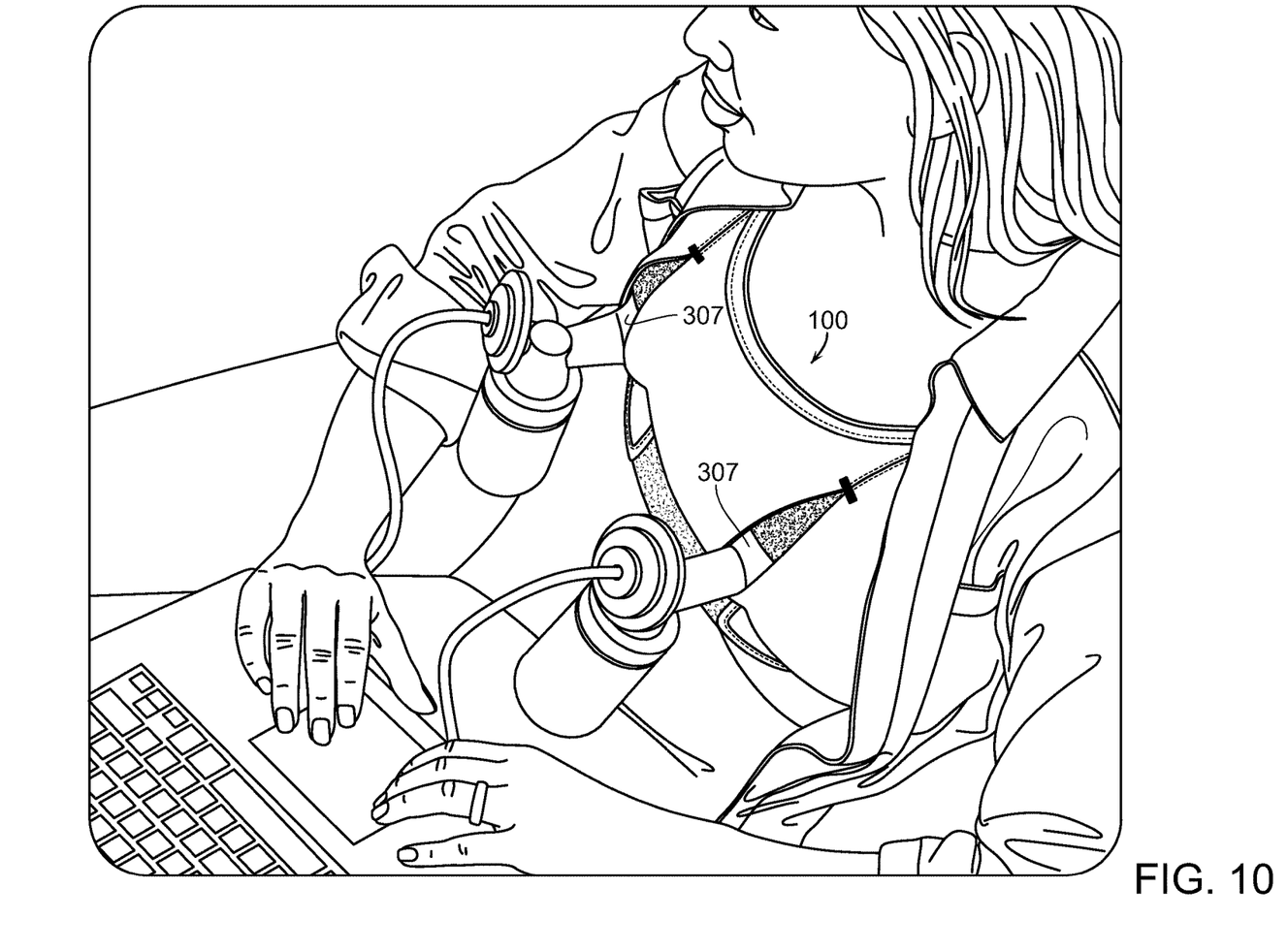
FIG. 10 is a depiction of environmental use of the garment, the compression device, and a breast pump.

Similarly, it is important that breast pads [301(L); 301(R)] stay in place without shifting, and even more important that they expand inward towards the breast when inflated. Thus, compression layer is comprised of a material with low elasticity such as Neoprene fabric or Fabric backed Foam. Moreover, holster [109] is located on compression layer centered between the breasts, so that the breast pads are further kept in place by the controller [402] and the controller becomes an additional barrier against which the bladders can push so as to provide adequate massage in the cleavage area of the breast. Of course, holster [109] lends added convenience to the device, as the breast pads and controller all conveniently rest within pocket [108]. Closure means [110; 111] allow the user to close the pocket [108] and wear while pumping, as depicted in FIG. 10. Closure means [110; 111] are depicted as buttons in FIG. 1, but may be any other types of closure devices such as hook-and-loop fasteners or zippers. Side zippers [112; 113] provide easy access to the breast pads while inside of the garment, so that they do not need to be removed or rearranged from the top of the pocket.

Adjustability is an important feature of the garment, because it ensures a proper fit, crucial to keeping the breast pads in place so that they expand inward towards the breast as designed. For instance, torso band [104] comprises closure means [105] and an adjustable strap [114] using hook-and-loop fasteners. Here, closure means [105] is a side release plastic buckle, but any other sturdy closure means may be used. Left [106] and right [107] shoulder straps are preferably also adjustable, here shown using foldover straps [115; 116] using hook-and-loop fasteners. Elastic side straps [117; 118] also hold the bust section of the garment closer against the body while worn, further ensuring that the breast pads stay in place.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention as defined by the following claims.

The invention claimed is:

1. An automated nursing system comprising:
   a left breast pad and a right breast pad, each breast pad comprising a C-shaped pad having an inner surface at a first material, the inner surface comprising a plurality of ridges, and an outer surface of a second material, wherein the inner and outer surfaces are sealed together at an inner circumference of the C-shaped pad, an outer circumference of the C-shaped pad, and along an entire length of at least two radii of the C-shaped pad, thereby forming exactly three fluid bladder sectors, each fluid bladder sector attached to a fluid supply tube at the outer surface, and wherein each sealing area separating the fluid bladder sectors has a width;
   a connection means for adjustably connecting the ends of the C-shaped pad together such that the pad forms a frustum for placement over the breast, the frustum having an angle that is adjustable by said connection means; and
   a massage controller comprising an electric pump and a plurality of solenoid valves connected to each fluid supply tube.

2. The automated nursing system of claim 1 further comprising:
   a nursing garment for receiving the left breast pad, the right breast pad, and the massage controller, comprising:
   a torso band fitting around a torso;
   a bust cover attached to the torso band, the bust cover comprising an inner panel and a compression panel, the inner panel and the compression panel secured together at the torso band such that the inner panel and the compression panel form a breast pocket for receiving the left breast pad, the right breast pad, and the massage controller, the breast pocket mouth being at the top of the bust cover; and
   a left adjustable shoulder strap attached to the top left of the bust cover and to the torso band; and a right adjustable shoulder strap attached to the top right of the bust cover and to the torso band.

3. The automated nursing device of claim 2 wherein the plurality of ridges on the inner surface of each breast pad are formed by thermoforming.

4. The automated nursing device of claim 3 further comprising a holster horizontally centered on the compression panel for receiving the massage controller.

5. The automated nursing device of claim 2 wherein the plurality of ridges are comprised of an elastic material and adhered to the inner surface.

6. The automated nursing device of claim 5 further comprising a holster horizontally centered on the compression panel for receiving the massage controller.

7. The automated nursing device of claim 2 further comprising a holster horizontally centered on the compression panel for receiving the massage controller.

8. The automated nursing device of claim 1 wherein the plurality of ridges on the inner surface of each breast pad are formed by thermoforming.

9. The automated nursing device of claim 1 wherein the plurality of ridges are comprised of an elastic material and adhered to the inner surface.

* * * * *

UNITED STATES PATENT AND TRADEMARK OFFICE
CERTIFICATE OF CORRECTION

PATENT NO. : 10,758,653 B2
APPLICATION NO. : 16/424766
DATED : September 1, 2020
INVENTOR(S) : Kumar et al.

Page 1 of 1

It is certified that error appears in the above-identified patent and that said Letters Patent is hereby corrected as shown below:

On the Title Page

Item (72), Inventor: add --Alexandra Looney, Wilmington, DE (US)--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*